United States Patent [19]

Pohl et al.

[11] Patent Number: 4,650,912
[45] Date of Patent: Mar. 17, 1987

[54] RECOVERY OF NITRIC ACID FROM NITRATION SPENT ACID BY TOLUENE EXTRACTION

[75] Inventors: Michael C. Pohl, Tucker, Ga.; Richard V. C. Carr, Allentown; John E. Sawicki, Breinigsville, both of Pa.

[73] Assignee: Air Products and Chemicals, Inc., Allentown, Pa.

[21] Appl. No.: 716,061

[22] Filed: Mar. 26, 1985

[51] Int. Cl.⁴ .............................................. C07C 79/10
[52] U.S. Cl. .................................... 568/934; 568/932; 568/927; 568/939; 568/940
[58] Field of Search ............... 568/934, 932, 939, 940, 568/935, 927

[56] References Cited

U.S. PATENT DOCUMENTS

| | | | |
|---|---|---|---|
| 2,773,911 | 12/1956 | Dubois et al. | 260/645 |
| 2,849,497 | 8/1958 | Buchanan | 260/645 |
| 4,257,986 | 3/1981 | Milligan et al. | 568/934 |
| 4,496,782 | 1/1985 | Carr | 568/934 |

Primary Examiner—John F. Terapane
Assistant Examiner—Susan Wolffe
Attorney, Agent, or Firm—Michael Leach; James C. Simmons; E. Eugene Innis

[57] ABSTRACT

In a method for denitrifying the nitric acid- and nitrous acid-containing spent acid phase from the nitration of an aromatic hydrocarbon by the mixed acid process which comprises forming a denitrification reaction medium by contacting the spent acid phase with an aromatic hydrocarbon under nitration reaction conditions to recover the nitric acid by the formation of a nitroaromatic hydrocarbon, the improvement which comprises (a) adding an amount of aromatic hydrocarbon which is slightly less than or equal to the stoichiometric amount necessary to deplete the spent acid phase of nitric acid, (b) photometrically monitoring the denitrification reaction medium for the appearance of a dark red to black color, and (c) upon detection of such color, adjusting the aromatic hydrocarbon:nitric acid molar ratio in the denitrification reaction medium to eliminate the color by reducing the aromatic hydrocarbon feed rate, or adding nitric acid to the denitrification reaction medium.

6 Claims, 1 Drawing Figure

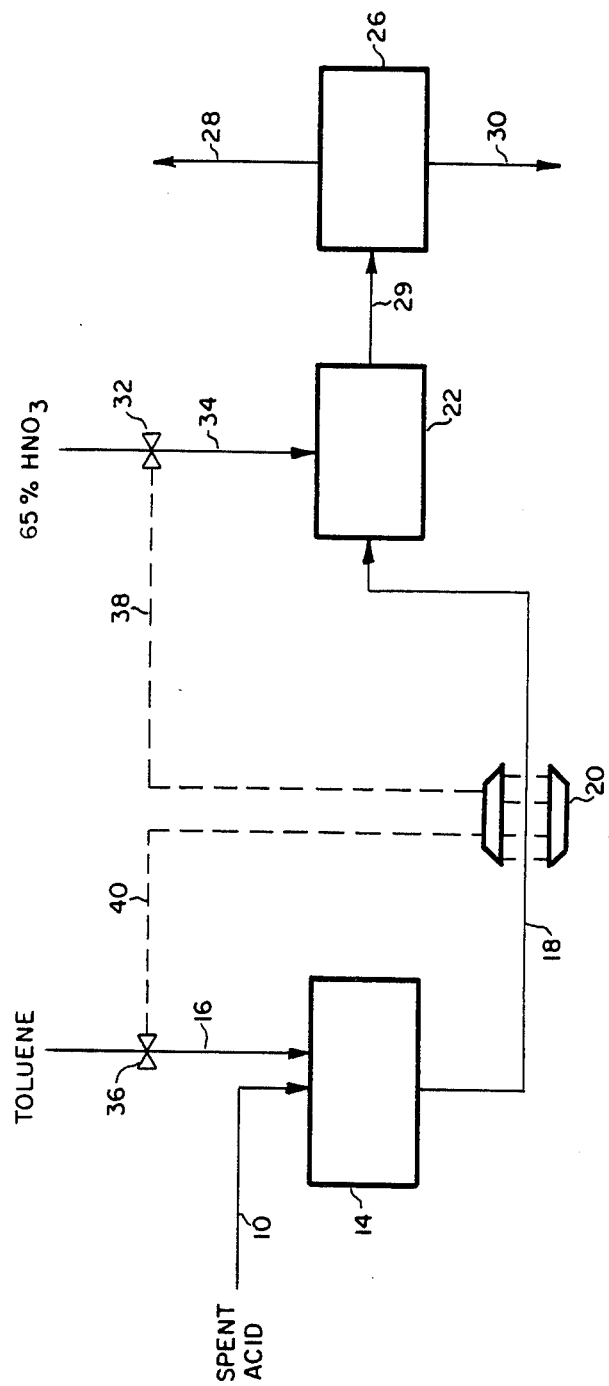

RECOVERY OF NITRIC ACID FROM NITRATION SPENT ACID BY TOLUENE EXTRACTION

TECHNICAL FIELD

The invention relates to a method for recovering nitric acid. More specifically, the present invention relates to a method for recovering the nitric acid content of a spent acid stream from the nitration of aromatic hydrocarbons.

BACKGROUND OF THE INVENTION

Commercial aromatic nitration processes are generally operated with the mixed acid system comprising sulfuric and nitric acids. A substantial amount of nitric acid is typically lost in an economically and environmentally unsound manner in the spent acid of nitration. For example, conventional dinitrotoluene processes comprise reacting toluene in a first nitration stage to form mononitrotoluene and separating the organic product from the aqueous spent acid phase. The nitric acid in the spent acid phase is usually removed or recovered so that the remaining sulfuric acid can be reconcentrated and recycled. The crude mononitrotoluenes are then nitrated with fresh nitrating acid in a second nitration stage. The dinitrotoluene product is then separated from the aqueous spent acid phase which is recycled to a nitration stage.

Ideally, the nitric acid in the aqueous spent acid of the mononitration stage should be recovered with a minimum of processing and with no risk of discoloration (charring) of the spent acid, i.e. the formation of what is known in the art as black spent acid. One such method involves the extraction of the spent acid with the aromatic hydrocarbon being nitrated in the process. This method removes the excess nitric acid from the spent acid in the form of the mononitro derivative of the aromatic hydrocarbon. Specifically, in a dinitrotoluene process, toluene is used to extract the spent acid to recover the nitric acid as mononitrotoluene in a post-reactor. It is recognized that extremely tight control over the stoichiometric reaction of the aromatic hydrocarbon is necessary to prevent formation of sulfuric acid soluble color bodies which render the final denitrified sulfuric acid black or dark red. It is believed that minor amounts of nitrous acid in the spent acid is responsible for the formation of the sulfuric acid soluble color bodies. The presence of nitric acid hinders or prevents this reaction. Thus, upon the depletion of the nitric acid when an excess of aromatic hydrocarbon is used to extract the spent acid phase in a denitrator, the nitrous acid reacts with the aromatic compounds to generate black spent acid. Such "charred" or black spent acid is unacceptable in the industry particularly if the denitrified spent acid is sent to a phosphate producer.

In another method, treatment of the spent acid of nitration with a variety of oxidizing or reducing agents which destroy the nitrous acid present in the spent acid prior to extraction with the aromatic hydrocarbon will prevent the formation of discolored sulfuric acid. The cost of these reagents precludes their use in the industry.

U.S. Pat. Nos. 2,773,911 and 2,849,497 are representative of the art disclosing the extraction/reaction of the nitric acid in the spent acid of nitration by contact with an aromatic hydrocarbon.

U.S. Pat. No. 4,257,986 discloses an improvement in a process for the manufacture of a nitroaromatic compounds produced by the mixed acid nitration method. The improvement resides in the refining of the aqueous acid mixture which comprises (a) contacting the spent mixed acid with an oxidizing or a reducing agent under conditions effective for removing contaminant nitrous acid, (b) contacting the aqueous spent acid mixture in step (a) with feed aromatic compound to remove contaminant organics and residual nitric acid and then, if necessary, (c) contacting the remaining nitric acid mixture with sufficient oxidizing agent under oxidizing conditions to remove residual organic components.

U.S. Pat. No. 4,496,782 assigned to the assignee of the present application discloses a method for denitrifying the aqueous spent acid of mononitration in which the nitric acid in the aqueous spent acid is recovered by adiabatically reacting greater than a stoichiometric amount of a mononitroaromatic hydrocarbon with the aqueous spent acid which has been fortified to a nitric acid concentration of at least about 2 wt%.

SUMMARY OF THE INVENTION

The invention provides a method for denitrifying the nitric acid- and nitrous acid-containing spent acid phase from the nitration of an aromatic hydrocarbon by the mixed acid process which denitrifying method comprises contacting the spent acid phase with an aromatic hydrocarbon, preferably the same hydrocarbon being nitrated, under nitration reaction conditions to recover the nitric acid by the formation of nitroaromatic hydrocarbon. The improvement comprises (a) forming a denitrification reaction medium by adding to the spent acid phase an amount of aromatic hydrocarbon which is slightly less than or equal to the stoichiometric amount necessary to completely recover the nitric acid and reacting the denitrification reaction medium under nitration reaction conditions, (b) photometrically monitoring the denitrification reaction medium for the appearance of a dark red to black color, and (c) upon detection of such color, adjusting the aromatic hydrocarbon:nitric acid molar ratio in the denitrification reaction medium to eliminate the dark red to black color by
  (i) reducing the feed rate of the aromatic hydrocarbon to the denitrification reaction medium, or
  (ii) adding an amount of nitric acid sufficient to eliminate the black color.

Following the denitrification reaction the mononitroaromatic hydrocarbon product is allowed to phase separate from the denitrified spent acid phase and is recycled to the nitration reaction process. The denitrified spent acid is then purified and concentrated in the usual fashion.

Thus, according to the present invention the formation of the black color in the spent acid phase is used as a feed-forward control to regulate the toluene feed to the denitrator or to add sufficient nitric acid to prevent the color formation.

Advantages of the toluene extraction method for recovering nitric acid according to the invention include the following:

A savings on raw material costs, an increase in plant capacity and a reduction in the waste volume generated;

The nitric acid is recovered as a useful product, i.e. in the form of the mononitroaromatic hydrocarbon which is a precursor to dinitration;

An energy savings over the mononitrotoluene extraction process;

A savings on the chemical costs of processes using materials to destroy the nitrous acid; and The operating costs are decreased since no oxidizing or reducing agents are required.

BRIEF DESCRIPTION OF THE DRAWING

The sole FIGURE is a schematic diagram of the two embodiments of the denitrification process according to the invention.

DETAILED DESCRIPTION OF THE INVENTION

The spent acid of nitration which can be denitrified according to the invention is any spent mixed acid phase from the nitration of an aromatic hydrocarbon. In other words, the spent acid phase may come from a mononitration stage in the production of mononitroaromatic hydrocarbons or in the two step nitration of aromatic hydrocarbons to dinitroaromatic hydrocarbons. The only requirement for the spent acid is that it contain sulfuric acid in a concentration of at least about 70 wt%. Most industrial mononitration stages are operated so that the spent acid phase also contains nitric acid at about 1 wt% or less, preferably less than about 0.4 wt%.

In a preferred embodiment the invention is incorporated into a process for dinitrating toluene which nitration process comprises (a) nitrating toluene in a first nitration stage with an aqueous mixture of sulfuric and nitric acids to form a mononitrotoluene containing organic phase and a first aqueous spent acid phase containing minor amounts of nitric acid and nitrous acid, (b) separating the organic phase from the first aqueous spent acid phase, (c) nitrating the mononitrotoluenes contained in the organic phase in a second nitration stage using a mixture of sulfuric and nitric acids to form dinitrotoluenes in the organic phase and a second aqueous spent acid phase, (d) separating the organic phase from the second aqueous spent acid phase, and (e) recovering dinitrotoluenes from the organic phase.

The method of the invention as applied to the above two stage dinitrotoluene process comprises (1) continually forming a denitrification reaction medium by adding to a continuous feed of first spent acid phase an amount of toluene which is slightly less than or equal to the stoichiometric amount necessary to totally deplete the spent acid phase of nitric acid, (2) reacting the denitrification reaction medium under nitration reaction conditions to yield a mononitrotoluene-containing organic phase, (3) photometrically monitoring the denitrification reaction medium to detect the appearance of a dark red to black color, and (4) upon detection of a dark red to black color, adjusting the toluene to nitric acid molar ratio in the denitrification reaction medium to eliminate the color by reducing the feed rate of toluene or adding nitric acid to the denitrification reaction medium, (5) separating the resulting mononitrotoluene-containing organic phase from the denitrified spent acid phase, and (6) recycling the organic phase of the mononitration reaction stage.

The molar amount of aromatic hydrocarbon which is added to the spent acid phase in forming the denitrification reaction medium should be about 0.9–1 moles per mole of nitric acid in the spent acid, preferably about 0.95–1.0 moles toluene/mole nitric acid, ideally equimolar.

The denitrification reaction medium is maintained under mononitration reaction conditions, for example at a reaction temperature from about 35° to 70° C., preferably about 50–60° C., and under about 1 atm pressure.

Suitable aromatic hydrocarbons for reaction with the nitric acid in the spent acid phase include benzene and alkyl-substituted benzenes such as t-butyl benzene, the isomers of xylene and the preferred toluene. It is also preferred to use the aromatic hydrocarbon which is nitrated in the process that provides the spent acid to be denitrified. In other words, if the spent acid for denitrification is generated in a process for dinitrating toluene, the spent acid is ideally contacted with toluene.

In the sole FIGURE the spent acid of nitration, for example from storage of mononitration stage spent acid, is introduced by line 10 into denitrification reaction vessel 14. Toluene in line 16 is also introduced into the vessel with agitation to provide a denitrification reaction medium which is maintained under nitration reaction conditions. Toluene is added at a rate to provide slightly less than or equal to the stoichiometric amount necessary to essentially deplete the nitric acid in the spent acid phase. Denitrification reaction medium effluent in line 18 passes through a spectrophotometer 20 adapted to detect photometrically the presence of a dark red to black color in the effluent. The denitrification reaction effluent passes into reactor vessel 22 having a relatively short residence time and then via line 24 into separator 26 where the reaction medium effluent separates into an organic upper layer and an aqueous lower layer. From the separator 26 the organic phase comprising mononitrotoluene (MNT) in line 28 is recycled to the nitration process and denitrified spent acid phase in line 30 is reconcentrated as typically performed in the art.

Should the amount of toluene in the denitrification reaction medium become greater than the stoichiometric amount necessary to react with the nitric acid in the spent acid phase as a result of (a) the nitric acid concentration in the spent acid received from line 10 decreasing or (b) the quantity of toluene received from line 16 increasing, sulfuric acid color bodies would appear in the denitrification effluent passing through line 18 rendering it a dark red to black color. Such color will be photometrically detected by spectrophotometer 20 which is electrically adapted to change the toluene:nitric acid molar ratio in the denitrification effluent stream to eliminate the color by either of two methods.

One such method of eliminating the color in the effluent stream is accomplished by electronically opening valve 32 via line 38 to permit 65% aqueous nitric acid to be mixed in a controlled rate with the effluent from line 18 in reaction vessel 22. The other method involves electronically closing valve 36 via line 40 to lessen the flow of toluene into the denitrification vessel 14.

Table 1 presents process stream flow data applicable to the scheme depicted in the FIGURE.

TABLE 1

| | STREAM FLOWS [lb/hr; (wt %)] | | | | | |
|---|---|---|---|---|---|---|
| | 10 | 16 | 18 | 34 | 28 | 30 |
| $HNO_3$ | 800 (0.5) | — | 184 (0.17) | 800 (65) | 4 (0.2) | 180 (0.1) |
| $HNO_2$ | 800 (0.5) | — | 800 (0.5) | — | 17 (1.0) | 783 (0.5) |
| $H_2SO_4$ | 115,350 (72.5) | — | 115,350 (72) | — | 20 (1.2) | 115,330 (73) |
| MNT | 634 (0.4) | — | 1940 (1.2) | — | 1294 (78) | 646 (0.4) |
| DNT | 160 (0.1) | — | 160 (0.1) | — | 107 (6.5) | 53 (0.03) |
| By-Products | — | — | 24 (0.02) | — | 12 (0.7) | 12 (0.01) |
| $H_2O$ | 41,400 (26) | — | 41,572 (26) | 430 (35) | 8 (0.5) | 41,564 (26) |
| Toluene | — | 1170 (100) | 285 (0.2) | — | 190 (11.5) | 95 (0.06) |
| TOTAL FLOW | 159,144 | 1170 | 160,315 | (Added only as needed) | 1652 | 158,663 |
| TEMPERATURE | 105 | | 115 | | 115 | 115 |
| PRESSURE | | | ATM | | ATM | ATM |

STATEMENT OF INDUSTRIAL APPLICATION

The process in this invention provides a means for denitrifying the spent acid of nitration from an industrial nitration process without losing a substantial amount of the nitric acid in the spent acid in an economically and environmentally unsound manner.

We claim:

1. In a method for denitrifying the nitric acid- and nitrous acid-containing spent acid phase from the nitration of an aromatic hydrocarbon by the mixed acid process which comprises forming a denitrification reaction medium by contacting the spent acid phase with an aromatic hydrocarbon under nitration reaction conditions to recover the nitric acid by the formation of a nitroaromatic hydrocarbon, the improvement which comprises (a) adding an amount of aromatic hydrocarbon which is slightly less than or equal to the stoichiometric amount necessary to deplete the spent acid phase of nitric acid, (b) photometrically monitoring the denitrification reaction medium for the appearance of a dark red to black color, and (c) upon detection of such color, adjusting the aromatic hydrocarbon:nitric acid molar ratio in the denitrification reaction medium to eliminate the color.

2. The method of claim 1 in which the aromatic hydrocarbon:nitric acid molar ratio is adjusted by reducing the feed rate of the aromatic hydrocarbon to the denitrification reaction medium.

3. The method of claim 1 in which the aromatic hydrocarbon contacted with the spent acid phase is toluene.

4. The method of claim 2 in which the aromatic hydrocarbon contacted with the spent acid phase is toluene.

5. The method of claim 1 in which the aromatic hydrocarbon:nitric acid molar ratio is adjusted by adding nitric acid to the denitrification reaction medium.

6. The method of claim 5 in which the aromatic hydrocarbon contacted with the spent acid phase is toluene.

* * * * *